US010123559B2

(12) United States Patent
Smith et al.

(10) Patent No.: US 10,123,559 B2
(45) Date of Patent: Nov. 13, 2018

(54) OZONE RAIN PAN

(71) Applicant: GUARDIAN MANUFACTURING, INC., Cocoa, FL (US)

(72) Inventors: Charles Smith, Merritt Island, FL (US); Thoram Charanda, Mount Dora, FL (US)

(73) Assignee: GUARDIAN MANUFACTURING, INC., Cocoa, FL (US)

( * ) Notice: Subject to any disclaimer, the term of this patent is extended or adjusted under 35 U.S.C. 154(b) by 11 days.

(21) Appl. No.: 15/641,048

(22) Filed: Jul. 3, 2017

(65) Prior Publication Data

US 2018/0007948 A1    Jan. 11, 2018

Related U.S. Application Data

(60) Provisional application No. 62/359,488, filed on Jul. 7, 2016.

(51) Int. Cl.
| | | |
|---|---|---|
| *B08B 3/04* | (2006.01) | |
| *A23N 12/02* | (2006.01) | |
| *A22C 17/08* | (2006.01) | |
| *A22C 21/00* | (2006.01) | |
| *A23B 4/00* | (2006.01) | |
| *A23B 7/00* | (2006.01) | |
| *A23L 3/00* | (2006.01) | |

(52) U.S. Cl.
CPC .............. *A23N 12/02* (2013.01); *A22C 17/08* (2013.01); *A22C 21/0061* (2013.01); *A23B 4/00* (2013.01); *A23B 7/00* (2013.01); *A23L 3/00* (2013.01); *B08B 3/04* (2013.01); *A23V 2002/00* (2013.01)

(58) Field of Classification Search
CPC ...... A23N 12/02; A23V 2002/00; A23B 4/00; A23B 7/00; A23L 3/00; A22C 17/08; A22C 21/0061; B08B 3/04
See application file for complete search history.

(56) References Cited

U.S. PATENT DOCUMENTS

| | | | | |
|---|---|---|---|---|
| 5,227,184 | A * | 7/1993 | Hurst ................. | A23B 4/24 |
| | | | | 426/312 |
| 5,494,576 | A * | 2/1996 | Hoppe ................ | C02F 1/325 |
| | | | | 210/198.1 |
| 5,582,717 | A * | 12/1996 | Di Santo ............ | B01D 61/08 |
| | | | | 210/192 |
| 6,120,822 | A * | 9/2000 | Denvir ............... | A23B 7/144 |
| | | | | 422/28 |
| 6,132,629 | A * | 10/2000 | Boley ............. | B01F 3/04985 |
| | | | | 210/167.11 |
| 6,551,182 | B2 * | 4/2003 | Caracciolo, Jr. .... | A22C 21/0061 |
| | | | | 452/81 |
| 6,644,043 | B2 * | 11/2003 | Later .................. | A23B 7/0433 |
| | | | | 62/100 |
| 7,470,172 | B2 * | 12/2008 | Carracciolo, Jr. ...... | |
| | | | | A22C 21/0061 |
| | | | | 452/81 |
| 8,696,796 | B2 * | 4/2014 | Gillette .............. | A23L 3/358 |
| | | | | 210/188 |

(Continued)

*Primary Examiner* — Alexander Markoff
(74) *Attorney, Agent, or Firm* — Kilpatrick Townsend & Stockton LLP; Kristin M. Crall (57) ABSTRACT

Embodiments of the present disclosure relate generally to systems and methods for combing ozone and water to deliver ozonated water in a rinse stream. The ozone rain pan finds particular use for rinsing food products traveling along a conveyor line with ozonated water.

20 Claims, 7 Drawing Sheets

(56) References Cited

U.S. PATENT DOCUMENTS

| | | | |
|---|---|---|---|
| 9,226,523 B2* | 1/2016 | Leech | A23L 3/28 |
| 9,924,727 B2* | 3/2018 | Massey | A23B 4/22 |
| 2002/0192110 A1* | 12/2002 | Garlick | A23B 4/24 |
| | | | 422/37 |
| 2003/0156978 A1* | 8/2003 | Gillette | A23L 3/358 |
| | | | 422/31 |
| 2005/0017380 A1* | 1/2005 | Namespetra | A61L 2/183 |
| | | | 261/75 |
| 2007/0157955 A1* | 7/2007 | Lin | A23B 7/152 |
| | | | 134/94.1 |
| 2008/0227680 A1* | 9/2008 | Lynn | B01F 3/04475 |
| | | | 510/370 |
| 2008/0292498 A1* | 11/2008 | Resch | A61L 2/22 |
| | | | 422/29 |
| 2009/0071331 A1* | 3/2009 | Gillette | A23L 3/358 |
| | | | 95/91 |
| 2012/0193303 A1* | 8/2012 | Hengsperger | C02F 1/20 |
| | | | 210/760 |
| 2015/0024096 A1* | 1/2015 | Leech | A23L 3/28 |
| | | | 426/248 |
| 2015/0157050 A1* | 6/2015 | Nicholson | A22C 21/0061 |
| | | | 452/177 |

\* cited by examiner

OZONE RAIN PAN

CROSS REFERENCE TO RELATED APPLICATIONS

This application claims the benefit of U.S. Provisional Application Ser. No. 62/359,488, filed Jul. 7, 2016, titled "Ozone Rain Pan," the entire contents of which are hereby incorporated by reference.

FIELD OF THE DISCLOSURE

Embodiments of the present disclosure relate generally to systems and methods for combining ozone and water to deliver ozonated water in a rinse stream. The ozone rain pan finds particular use for rinsing food products traveling along a conveyor line with ozonated water.

BACKGROUND

Ozonated water can be useful for disinfecting produce. Ozone can kill some of the microorganisms that would otherwise destroy the produce during storage. Current systems that use ozonated water for washing produce use spray head assemblies, also referred to as spray jets. In use, there is generally provided a pressurized pipe that delivers ozonated water into the processing area. Spray heads may be periodically positioned along the pipe (a) and/or a T-bar may be used for water delivery. Due to the gaseous nature of ozone, tests have found that spray jets can cause a loss of up to 70% or more of the dissolved ozone from the dosing source stream. For example, if the desired ozone level delivered to the product is 2 ppm, ozone generally needs to be dosed and run at levels up to 10 ppm in order to accommodate the atmospheric spray loss experienced due to the high to low pressure transition from the main supply line to the spray nozzle. Additionally, the amount of time the product is actually being dosed with the ozonated spray water is very short, typically for only a matter of 1-2 seconds. Further, because of potential ozone off-gassing in the vicinity of personnel, it is desirable to limit the amount of ozone lost from the ozonated water spray for safety reasons. Accordingly, improved methods for delivering ozonated water are desirable.

BRIEF SUMMARY

Embodiments of this disclosure thus provide systems and methods for delivering an ozone product, such as ozonated water, to a desired location. One example provides an ozone rain pan, comprising a water containment portion with at least one ozonated water inlet, a plurality of openings on a lower surface of the water containment portion; and an ozone destruct outlet. There may be provided an exhaust fan for removing off gassed air from ozonated water held in the water containment portion. The ozone rain pan may have one or more air openings for allowing fresh air to enter the water containment portion and/or a lid positioned over the water containment portion. The ozone destruct outlet may be positioned on the lid.

A further example provides a baffle system. The baffle system may include a plurality of baffles over and under which incoming ozonated water is caused to flow. A specific embodiment provides a series of three baffles, (a) a first baffle secured to the lower surface of the water containment portion and defining a first channel between a water containment portion sidewall and the first baffle, (b) a second baffle adjacent to the first baffle, the second baffle having a raised configuration such that water may pass thereunder, and (c) a third baffle adjacent to the second baffle, the third baffle secured to the lower surface of the water containment portion and having a height that is shorter than the first baffle. In this embodiment, incoming water collects in the first channel, flows over the first baffle, flows under the second baffle, and flows over the third baffle to enter a central holding portion of the water containment portion. The first baffle may optionally have a plurality of openings.

Another feature that may be provided is an overflow management system. The overflow management system may be an overflow wall and an overflow exit opening. The rain pan may include a system for mounting the water containment portion with respect to a conveyor. This mounting system may be one or more adjustable legs. Alternatively, this mounting system may be a shower head-like mount.

In use, the plurality of openings allow a rain stream of ozonated water to fall on one or more food products. It is possible to mount the ozone rain pan in a processing area for treatment of produce. It is possible to mount the ozone rain pan in a processing area for treatment of poultry or meat products. Other options as possible and considered within the scope of this disclosure.

A further embodiment disclosed provides a method for delivering a rain stream of ozonated water, comprising (a) mounting the disclosed ozone rain pan over a treatment zone; and (b) delivering ozonated water into at least one of the inlets of the ozone rain pan.

DETAILED DESCRIPTION

As part of the microbiological control strategy of a food product processing plant (including quality assurance and quality control), ozone is a key technology for the intervention and destruction of microorganisms such as bacteria, viruses, yeast, mold or other species to be controlled. The ozone rain pan described herein is designed to dose food products with a complete coverage of ozonated water for disinfection. The ozone rain pan may be used in conjunction with produce (such as apples, pears, cantaloupes, cherries, grapes, and any other produce types). In other examples, the ozone rain pan may be used in conjunction with other food products, such as poultry, meats, or any other options. Any products that may benefit from ozonated water treatment may be treated using the systems and methods described herein. In the described examples, ozonated water is allowed to "rain" on the product, allowing a longer contact time and eliminating much of the atmospheric off gas related to the use of spray jets.

One goal of the ozone rain pan is to address the need for achieving the required concentration times time (CT in units of mg-min/L) values for greater than 3-log kill of the common problematic microorganisms found in food processing plants (*Listeria m., e. coli, salmonella* and *campylobacter*). The ozone rain pan achieves this by directly dosing the product moving on a conveyor system through a constant shower of highly ozonated water. The distance over which the food product is dosed may span two or more linear feet. The dosing distance may be dependent upon the dimensions of the ozone rain pan body. In one specific example, the distance may be less than two feet, such as ½ foot to one foot or even less, depending upon design and treatment needs. In other examples, the distance may be greater than two feet, such as up to 3-6 feet or even longer. In many instances, the conveyor may have a brush head which causes a revolution of the produce or other food products being treated. The length of the ozone rain pan treatment zone may be modified such that the product being treated is generally treated on all sides, along a full rotation/revolution. (If the system is used to treat cantaloupe, it is generally expected that the treatment zone may be designed to be longer than the treatment zone length needed if the system is used to treat cherries, for example.)

Figure 1:
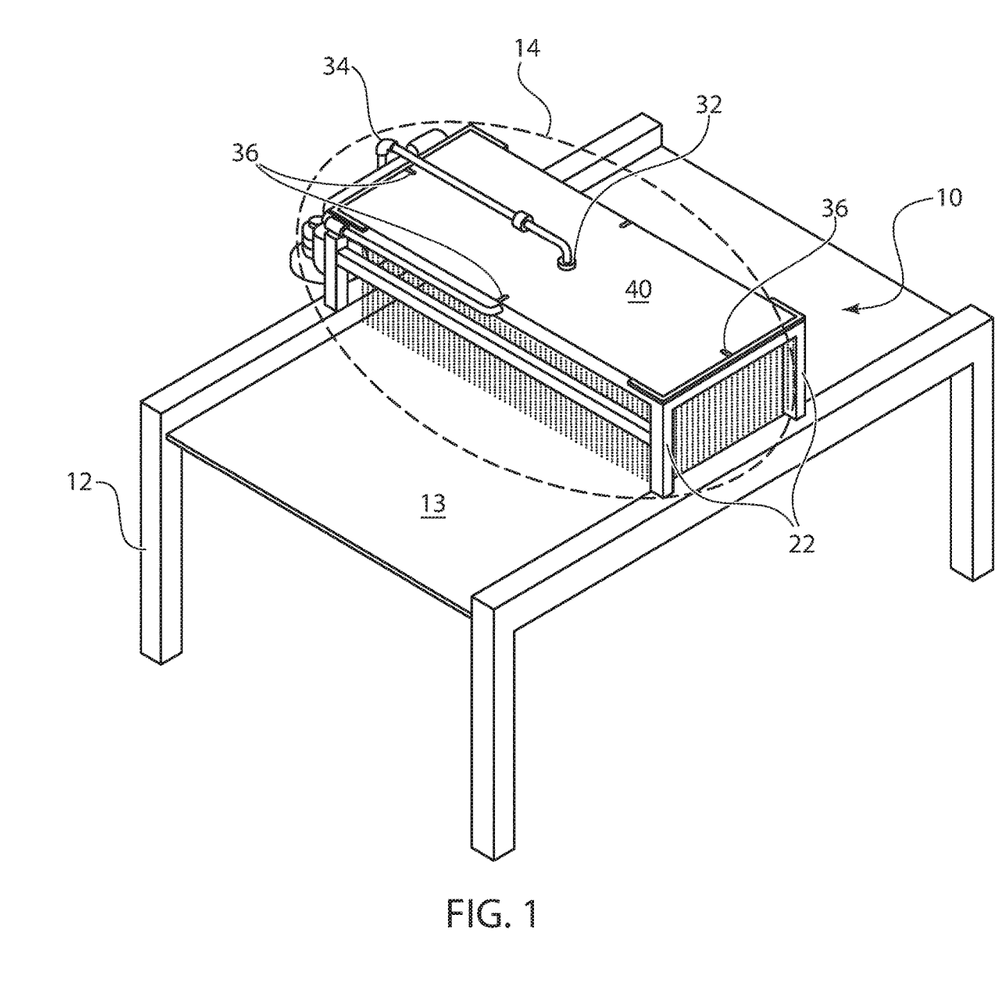
FIG. 1 shows a side perspective view of an ozone rain pan mounted on a conveyor system.
Figure 2:
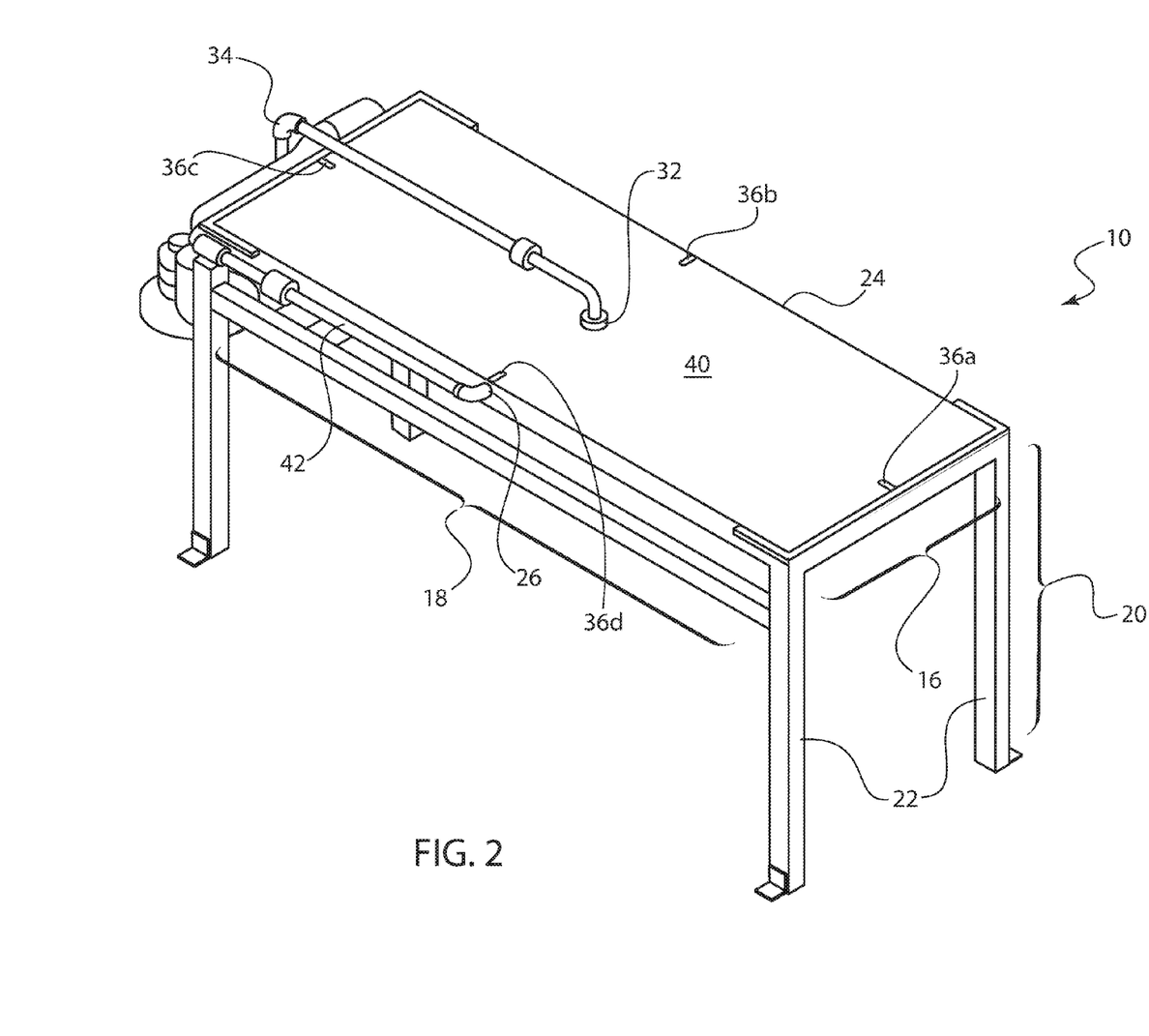
FIG. 2 shows a side perspective view of an ozone rain pan.

As illustrated by FIG. 1, the ozone rain pan 10 may be positioned atop a conveyor system 12. For example, the rain pan 10 may be directly mounted to the conveyor system 12. This configuration is provided as an example only. It should be understood, however, that the ozone rain pan 10 may be positioned in any location that allows an ozonated water stream to be directed as desired. For example, the rain pan 10 may be mounted above the conveyor, like a rain shower head. The rain pan 10 may be mounted to the ceiling of the treatment space or on a separate mounting scaffold. As food products are moved along the belt 13 of the conveyor system 12, they reach an ozone treatment zone 14. The length of the ozone treatment zone 14 may be dictated by the length 16 of the ozone rain pan 10. As illustrated by FIGS. 1 and 2, the distance across the ozone treatment zone 14 is generally dictated by the width 18 of the ozone rain pan 10. This width 18 is generally designed to correspond to the width of the conveyor belt 13. Conveyors are generally about three to six feet wide, so it is generally envisioned that the ozone rain pan 10 will correspond thereto. The height 20 of the ozone treatment zone 14 is dictated by the height of legs 22 of the ozone rain pan 10. The legs 22 may be designed such that the height 20 of the ozone treatment zone 14 corresponds to the food product being treated. It is desirable that the "rain" of ozonated water from the rain pan 10 be close enough to the food product that treatment be effective. The legs 22 are generally provided as a means to mount the water containment portion with respect to the conveyor.

In one specific example, the legs 22 may be about 10 to 16 inches high. In another specific example, the legs 22 may be made to be adjustable, such that the height of the ozone treatment zone may be adjusted based on the food product being treated. The adjustability may be provided by any appropriate system, such as ball and detent adjustability, telescoping legs, or any other appropriate option. The adjustability may be provided by leveling feet. In another example, there may be provided a single leg, which functions as a bracket to secure the ozone rain pan 10 directly to one side of the conveyor system 12. It is also possible for the ozone rain pan 10 to be mounted to a wall or other structure.

The bracket of the rain pan 10 may be designed to swivel so that the rain pan can be moved to address multiple nearby conveyor systems 12.

Although not shown, another means for mounting the water containment portion of the rain pan with respect to the conveyor may be a showerhead-like mount. The mount may allow the rain pan to be moved up and down with respect to the conveyor. The mount may allow the rain pan to be mounted above the conveyor. The mount may be telescopable, expandable with scissor-like arms, may be positioned on a mechanical arm, or another other option. The mount may allow the rain pan to be raised and lowered and optionally locked in place. The general intent is to position the ozone rain pan in close proximity to the item(s)/product(s) to be treated.

Figure 3:
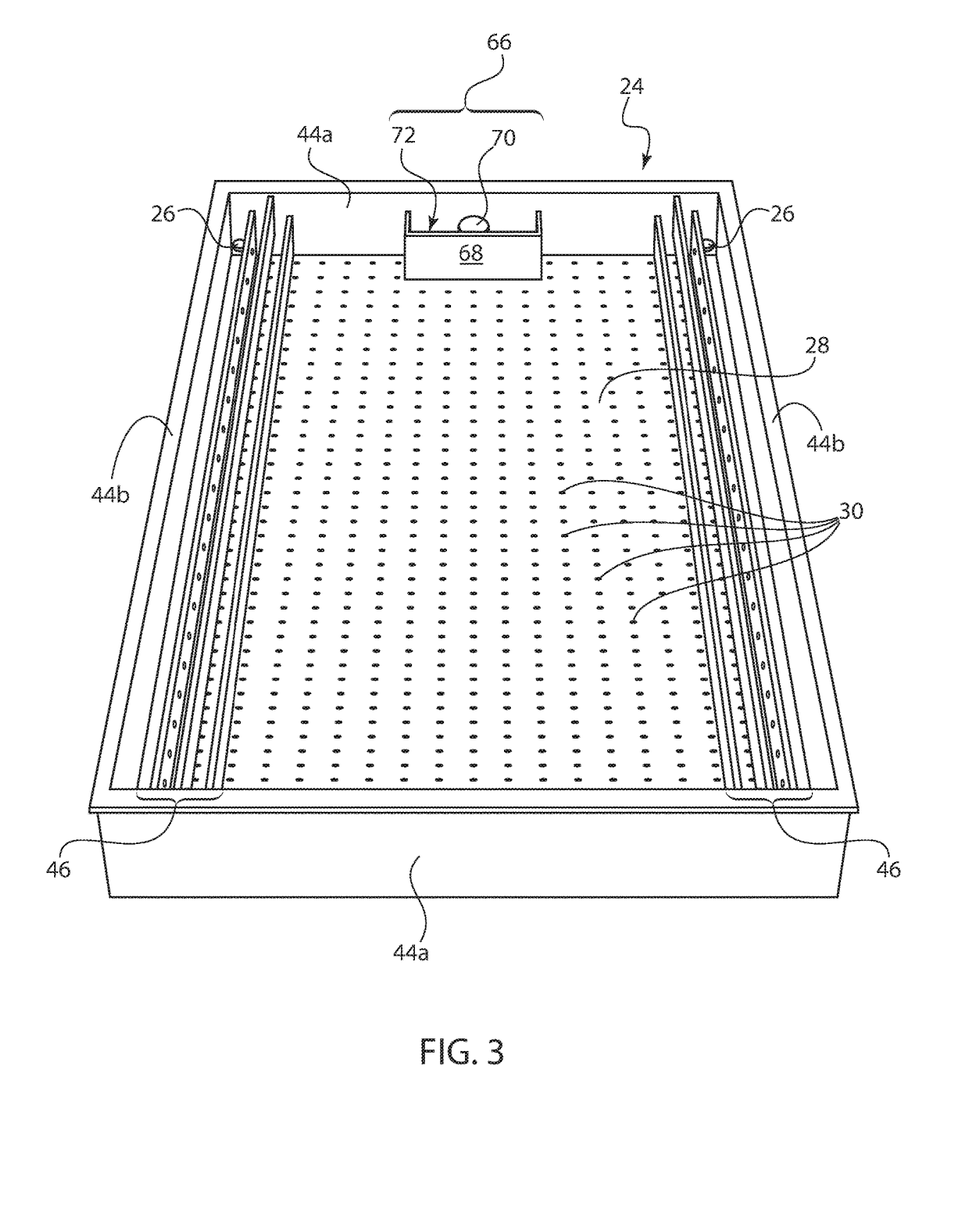
FIG. 3 shows a top perspective view of an alternate ozone rain pan with the lid removed.

The ozone rain pan 10 is generally provided as having a water containment portion 24. The water containment portion 24 has a lid 40 that encloses the entire flooded area of ozonated water as it enters from the ozone skid. FIG. 3 illustrates a water containment portion 24 with the lid 40 removed. In use, ozonated water is delivered directly into the water containment portion 24 via an inlet 26. The inlet 26 is generally shaped to receive the end of a water delivery conduit 42, such as a one or two inch diameter water hose or pipe. These dimensions, of course, may be altered as appropriate. In use, ozonated water flows into the water containment portion 24 of the pan via one or more inlets 26. (Ozone is injected into the water at an ozone generator area separate from the ozone rain pan described.)

More specifically, the water containment portion 24 is defined by a series of sides 44. The sides 44 may have any appropriate dimensions, depending upon the size of the water containment portion 24 for the intended use. In one specific example, the end sides 44*a* may be about 3 to 8 inches high and about 2 to 4 feet long. Elongated sides 44*b* may also be about 3 to 8 inches high and about 1 to 8 feet long. In a specific example, sides 44*a* and elongated sides 44*b* are about 4-5 inches high. The sides 44*a* may be about 3 feet long, and the elongated sides 44*a* may be about 3-8 feet long. An inlet 26 is positioned on at least one of the sides 44. It is possible to have more than one inlet 26 provided in order to define more than one ozonated water entry point. In FIG. 3, two inlets 26 positioned along the side 44*a* to define a left inlet and a right inlet. More or fewer inlets 26 are possible.

Figure 4:
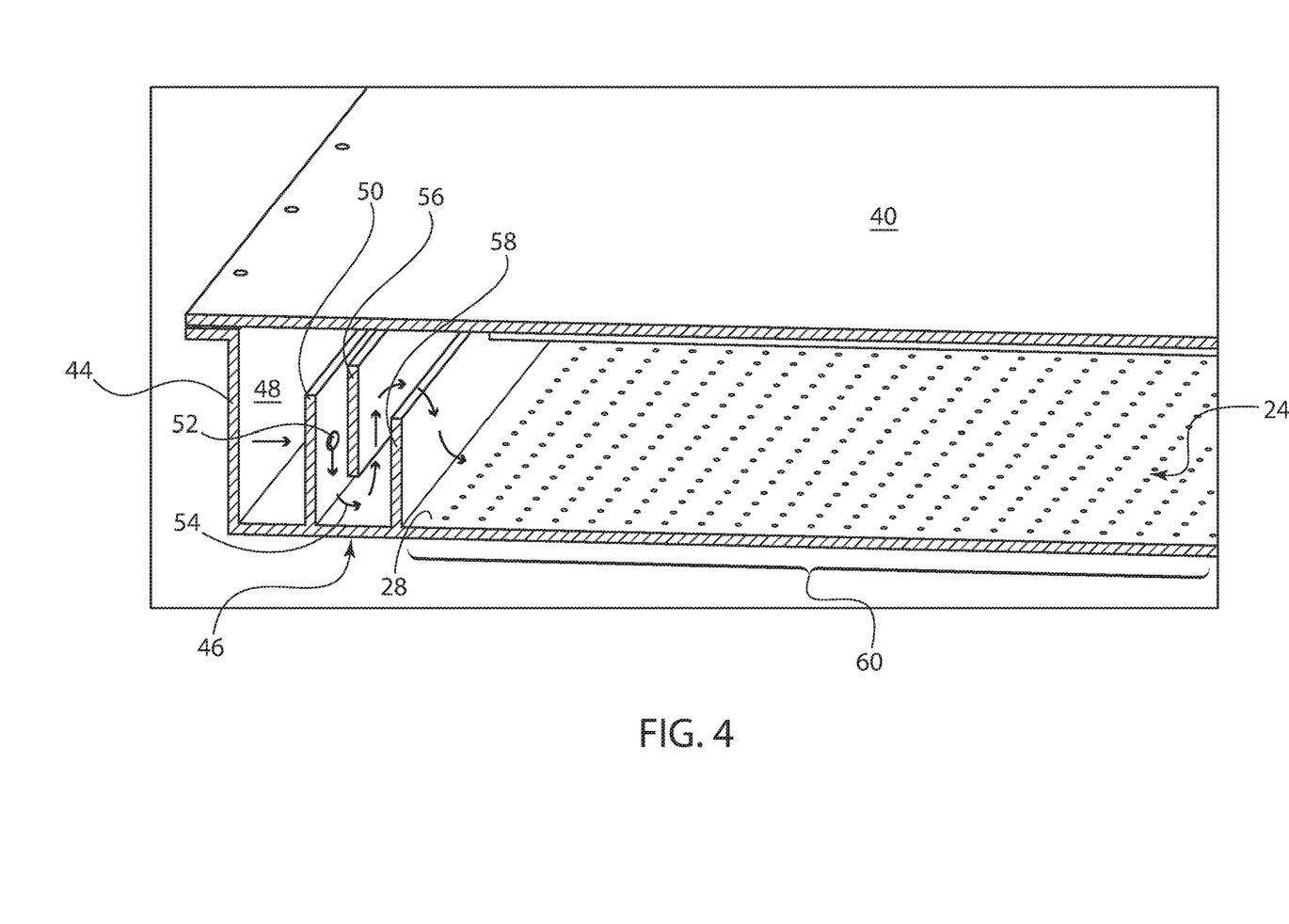
FIG. 4 shows a side cutaway view of an ozone rain pan, illustrating a baffle system.

Water containment portion 24 may also include a baffle system 46. FIG. 3 illustrates two sets of baffle systems 46, one along each elongated side 44*b*. One benefit of providing a baffle system 46 is to help maintain an even water flow within the water containment portion 24. A sectional side perspective view of baffles 46 is illustrated by FIG. 4. In use, delivery of water into inlet 26 initially allows water to pool in a first channel 48. The first channel 48 is bounded by a sidewall 44 and a first baffle 50. First baffle 50 is secured to the lower surface 28. Water collecting in the channel 48 is allowed to flow through optional openings 52 in the first baffle 50, once it reaches the height of openings 52. If water is delivered into first channel 48 more quickly than the openings 52 can filter, it is possible for water to flow over the top of first baffle 50. Once past the first baffle 50, water may then enter flow channel 54. Flow channel 54 moves underneath a second baffle 56 and over third baffle 58. (Although the second baffle 56 appears to be floating, it will be welded or otherwise secured to one of the sidewalls 44. The third baffle 58 is welded to the lower surface 28.) In a specific embodiment, the third baffle 58 has a shorter height than the first baffle 50. When water reaches the top of the third baffle

58, it is allowed to waterfall thereover, following the arrows of the flow channel 54. The purpose of baffle system 46 is to manage the influx of water into the central holding portion 60 of the water containment portion 24 of the ozone rain pan 10, as described further below.

The lower surface 28 of the ozone rain pan 10 has a plurality of openings 30 which are designed to allow the water contained in the central holding portion 60 of the containment portion 24 to "rain" out. The size of the openings 30 may be modified as necessary. They are generally sized such that water may collect in the containment portion 24 at about ½ to about ¾ inch of water level. The openings 30 may be positioned in a generally regular pattern. For example, FIG. 4 illustrates openings 30 as having a grid-like pattern. In other examples, the openings 30 may be positioned in irregular or other shaped patterns. The openings may be circular openings, similar to a rain-like showerhead. The openings may be elongated slits. The openings may be any other appropriate shape.

The baffle system 46 and the openings 30 cooperate together in order to deliver a study in constant "rainfall" of water leaving the ozone rain pan for example. Providing a baffle system 46 can be useful because it manages and otherwise slows the influx of water from the inlet 26 into the central holding portion 60. If all water is delivered at once, a stronger flow or "rainfall" stream may be experienced along edges of the rain pan, or through openings that are closest to an inlet. By allowing incoming water to pool in the first channel 50 and then to flow through flow channel 54, a more even stream of water may be delivered across the entire width of the rain pan. Additionally, the size of the openings 30 may be optimized for the size of the rain pan and the desired flow rate to be achieved. In some examples, the openings 30 may range from about 0.02 inches to about 0.08 inches in circumference. In a specific example, the openings 30 are about 0.05 inches in circumference. The openings 30 may be spaced apart from one another as desired for treatment. In one example, the spacing may range from about 0.5 inches to about 1.5 inches between a center of one opening to a center of an adjacent opening. In a specific example, the centers of the openings are spaced about 1 inch from one another.

In some instances, it may be possible for the water containment portion 24 to become overflowed. In order to manage this possibility, the central holding portion 60 is provided with an overflow management system 66, illustrated by FIG. 3. The system includes an overflow wall 68 and an overflow exit opening 70. If the water in the central holding portion 60 rises above the top of the overflow wall 68, the water will begin to flow into the interior space 72 created between the overflow wall 68 and the sidewall 44. Excess water may then exit through the overflow exit opening 70, which is formed as an opening in the sidewall 44. Overflow exit 70 may cooperate with tubing or other water delivery conduit. It is possible for the water to be rerouted back into one of the inlets 26. In another example, it is possible for the excess water to be routed elsewhere for other uses.

Figure 5:
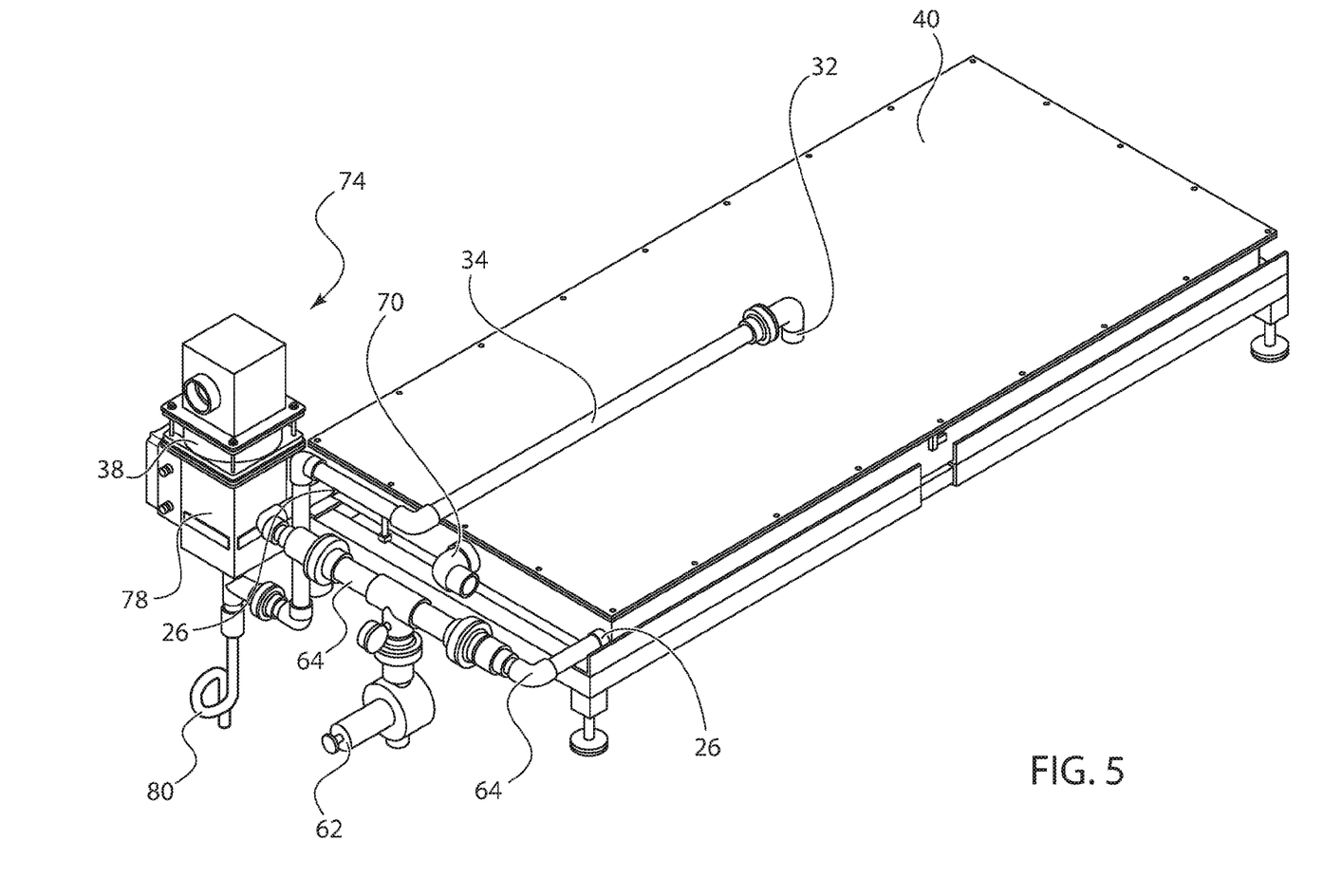
FIG. 5 shows a side perspective view of an ozone rain pan, illustrating the exhaust fan and ozone destruct system.

FIG. 5 illustrates a side view of the ozone rain pan 10. This figure illustrates that two inlets 26 may cooperate with a single ozonated water inlet 62, which splits into left and right conduits 64 to feed left and right inlets 26. The water inlet 62 may be provided with a pressure regulator. The pressure in the water delivery conduit 64 that cooperates with the inlets 62 and 26 for delivery of water into the ozone rain pan may be similar to the pressure used in an overhead pressurized ozonated water pipe for a storage room. For example, the pressure in the water conduit delivering the ozonated washer may be about 20 psi or less. Pressure may be varied in order to meet the ozonated water delivery requirements. Water pressure may be varied to speed or slow the delivery of water. The water is generally ozonated upstream of the water inlet 62 via an ozone generator. Exemplary ozone generators for this purpose are manufactured and sold by Guardian Manufacturing, Inc., of Cocoa, Fla.

FIG. 5 also illustrates one example of an exhaust duct system 74 that may be used to channel ozonated air out of the water containment portion 24 to an ozone destruct system. In one example, an exhaust fan 38 may be used to pull ozonated air from the water containment portion 24. The lid 40 may be provided with an ozone destruct outlet 32. Although illustrated as positioned at an upper/lid surface of the water containment portion 24, it is possible for the ozone destruct outlet 32 to be positioned anywhere along the water containment portion 24. In one example, the pressure in the water containment portion 24 is just slightly above atmospheric pressure. Suction from the exhaust fan 38 is very slight, just enough to remove the ambient air/ozonated air combination out through outlet 32. In one specific example, the pressure may be about −0.1 psi. Air leaving outlet 32 travels through conduit vent pipe 34 to the destruct unit 78. The destruct unit 78 also has a condensate drain 80.

FIGS. 1 and 2 illustrate a rain pan embodiment with a series of air holes 36 in the ozone rain pan 10. FIG. 2 shows an example having four air holes 36a-d, one positioned along each edge of the pan. This is provided as example only; it should be understood that air holes 36 may be positioned anywhere appropriate. In use, the air holes 36 allow a small amount of fresh air to be pulled into the water containment portion 24. In other embodiments, specified air holes may not be present, but fresh air is allowed to enter the top of the rain pan via the overflow exit opening/port 70 on the side of the pan. This fresh air is allowed to mingle with any off-gassed ozonated air that may rise from the water in the pan, all of which is collectively pulled out through the ozone destruct outlet 32. The exhaust fan 38 will pull the air and the small amount of ozone off gas from within the rain pan containment portion and send it through a catalytic destruct unit that will convert the ozone back into pure oxygen. This will ensure a safer work environment for the plant's employees, because the potential level of gaseous ozone is nearly eliminated.

Figure 6:
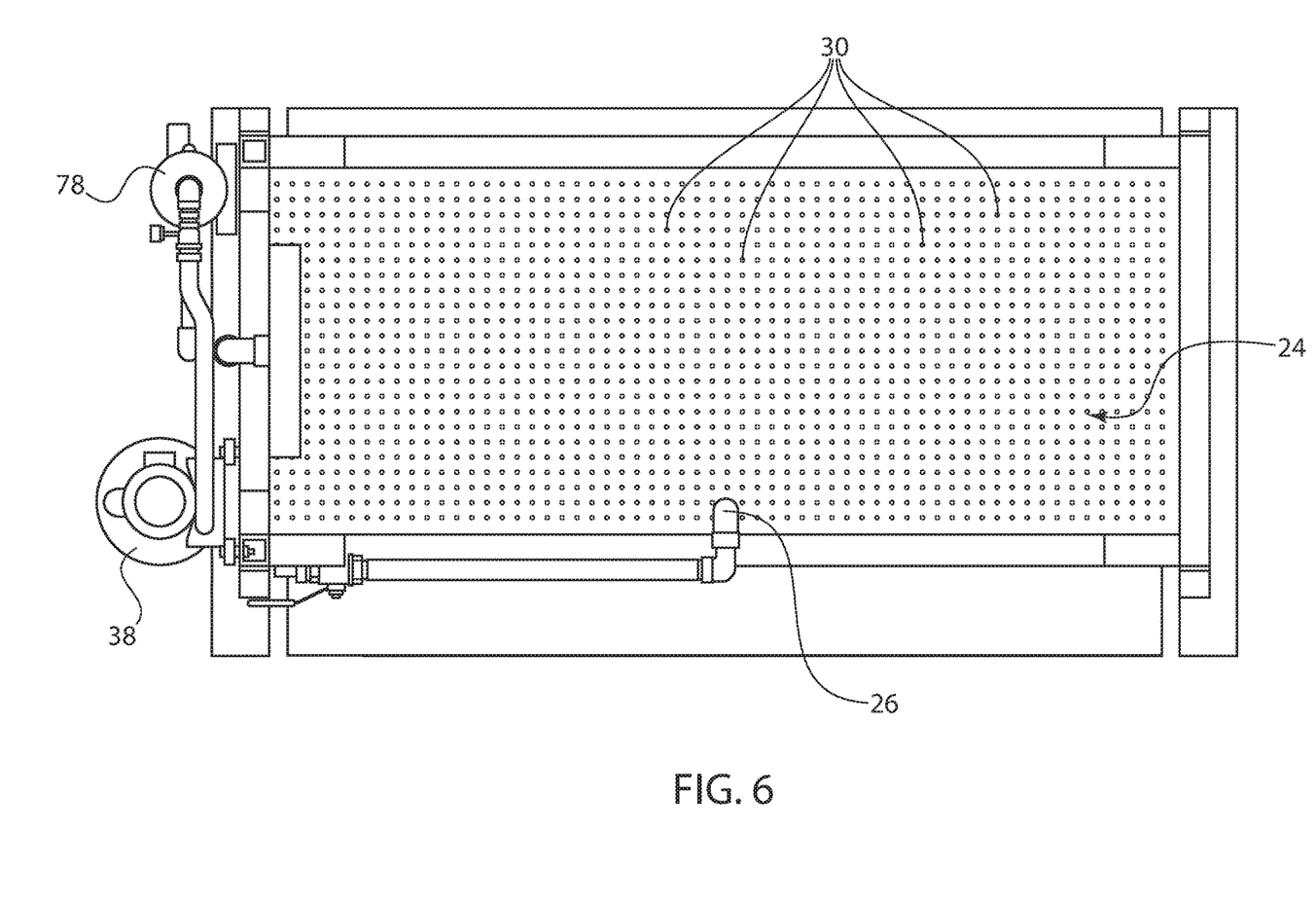
FIG. 6 shows a top plan view of the ozone rain pan of FIG. 2.
Figure 7A:
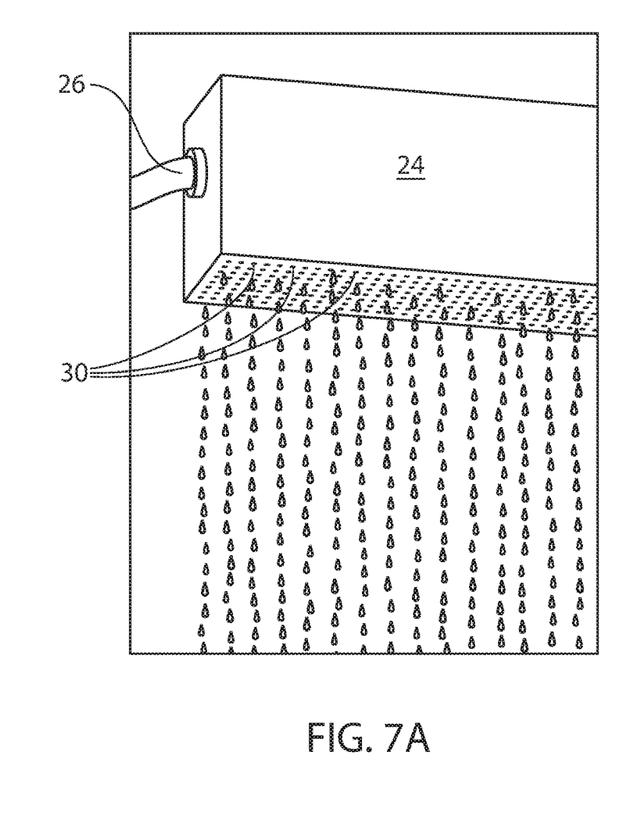
FIGS. 7A and 7B illustrate side views of an ozone rain pan in use.
Figure 7B:
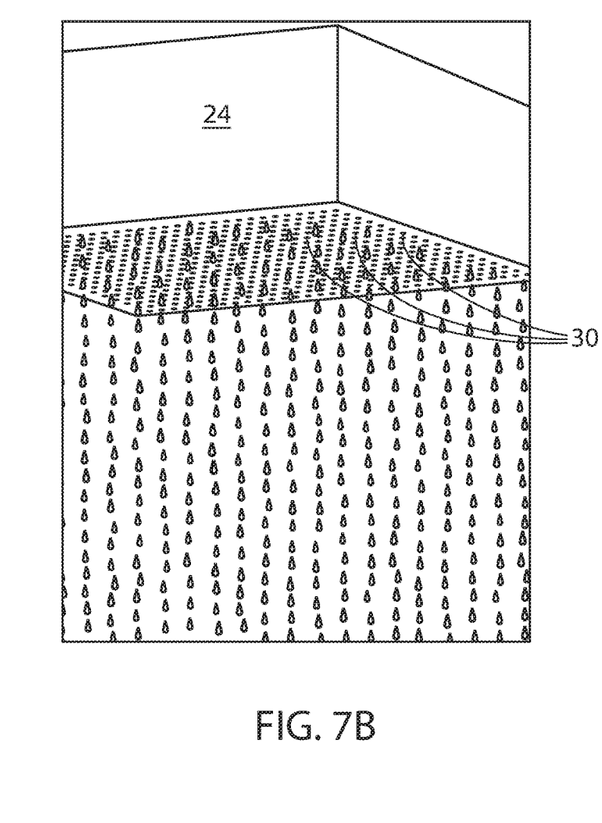

FIG. 6 illustrates a top plan view of the ozone rain pan of FIG. 2 with the lid removed. This embodiment illustrates an inlet 26 along one of the elongated sidewalls. This embodiment also illustrates a separate exhaust fan and destruct system, although it is possible for the systems to be stacked, as illustrated by FIG. 5.

The ozone rain pan 10 described herein is a significant improvement upon the more traditional use of spray jets. Due to the gaseous nature of ozone, spray jets can cause a loss of 70-80% or more of dissolved ozone from the dosing source stream. Additionally, the amount of time the product is actually being dosed with the ozonated spray water is very short, typically for only a matter of 1-2 seconds. Conversely, using the ozone rain pan described herein, the product will experience a continuous dose of ozonated water for longer. In specific examples, the treatment time may be more than 6 seconds (depending on the product conveyor speed, the length of the ozone rain pan, the size of the openings, and other modifiable parameters). In general, the ozone rain pan described allows 5-10 seconds of water treatment. If desired, even longer water treatment times may be achieved.

Ozone off gas can be a significant safety issue within a processing plant environment. The ozone rain pan disclosed herein will not create off gas from the dissolved ozone to the high extent that water spray jets do, due to the very low pressure drop of the ozonated water as it falls through the holes of the pan onto the product to be treated below. This substantially reduces the ozone off gas entering the work area, unlike the typical spray jet design. Additionally, the ozone rain pan includes a lid that will enclose the entire flooded area of ozonated water as it enters from the ozone skid. Connected to the lid is a pipe that goes to an exhaust fan that will pull air and the small amount of ozone off gas from within the rain pan and send it through a catalytic destruct unit that will completely convert the ozone back into pure oxygen. This will ensure a significantly safer work environment for the plant's employees as the potential level of gaseous ozone is nearly eliminated.

Changes and modifications, additions and deletions may be made to the structures and methods recited above and shown in the drawings without departing from the scope or spirit of the disclosure or the following claims.

What is claimed is:

1. A system for delivering ozonated water to an ozone treatment zone, the system comprising:
    an ozone rain pan box defining a lower surface, side walls connected to the lower surface, and a lid configured to be positioned over the side walls to define a water containment portion within the ozone rain pan in use,
    a plurality of openings spanning the lower surface, the plurality of opening sized and configured to allow water to flow therethrough via rainfall;
    a baffle that defines a channel between the baffle and one of the side walls; and
    at least one ozonated water inlet positioned to deliver ozonated water into the channel.

2. The system of claim 1, wherein the side walls comprise two end side walls and two elongated side walls to define a rectangular ozone rain pan.

3. The system of claim 1, wherein the side walls are between about 3 inches to about 8 inches high.

4. The system of claim 1, wherein the plurality of openings range in size from about 0.02 inches to about 0.08 inches in diameter.

5. The system of claim 1, wherein the plurality of openings are spaced from about 0.5 inches to about 1.5 inches between a center of one opening to a center of an adjacent opening and are arranged in a grid-like pattern.

6. The system of claim 1, wherein the baffle is secured to the lower surface of the ozone rain pan and comprises baffle openings therethrough, wherein water collecting in the channel flows through the baffle openings or over the baffle or both, depending upon speed of water delivery.

7. The system of claim 6, further comprising a second channel bounded by the baffle and a second baffle, wherein the second baffle is mounted between opposite side walls to form a flow channel under the second baffle.

8. The system of claim 7, further comprising a third channel bounded between the second baffle and a third baffle secured to the lower surface of the ozone rain pan, wherein water from the flow channel flows over the third baffle.

9. The system of claim 1, wherein the at least one ozonated water inlet comprises a first inlet positioned to deliver water to a channel located on one side of the water containment portion, and a second inlet positioned to deliver water to a second channel located on an opposite side of the water containment portion.

10. The system of claim 1, further comprising a water overflow management system comprising an exit opening in one of the side walls that is bounded by an overflow wall.

11. The system of claim 1, wherein the baffle comprises a baffle system positioned within the interior water containment portion, the baffle system comprising a plurality of baffles over and under which incoming ozonated water is caused to flow prior to entering a central water holding portion.

12. The system of claim 1, wherein the baffle comprises a baffle system that comprises a series of three baffles, (a) a first baffle secured to the lower surface of the water containment portion and defining a first channel between a water containment portion sidewall and the first baffle, (b) a second baffle adjacent to the first baffle, the second baffle having a raised configuration such that water may pass through a flow channel defined thereunder, and (c) a third baffle adjacent to the second baffle, the third baffle secured to the lower surface of the water containment portion and having a height that is shorter than the first baffle.

13. The system of claim 12, wherein incoming water collects in the first channel, flows over or through the first baffle, flows under the second baffle, and flows over the third baffle to enter a central holding portion of the water containment portion.

14. The system of claim 1, further comprising an ozone destruct outlet fluidly cooperating with the ozone rain pan.

15. The system of claim 14, wherein the ozone destruct outlet is positioned on the lid.

16. The system of claim 1, further comprising an ozone destruct unit for treating removed off gassed air.

17. The system of claim 1, further comprising one or more air openings in the side walls or lid for allowing fresh air to enter the interior water containment portion.

18. The system of claim 1, further comprising adjustable legs or a shower head-like mount for mounting the ozone rain pan with respect to a conveyor.

19. A method for delivering a rain stream of ozonated water to an ozone treatment zone, comprising:
    (a) mounting an ozone rain pan of claim 1 over the ozone treatment zone; and
    (b) delivering ozonated water into the at least one inlet of the ozone rain pan.

20. The system of claim 1, wherein the plurality of openings allow ozonated water to rain out from the ozone rain pan via gravity.

* * * * *